United States Patent [19]
Bailey, Jr.

[11] Patent Number: 5,213,114
[45] Date of Patent: May 25, 1993

[54] OPHTHALMOLOGIC DRAPE AND METHOD

[76] Inventor: Paul F. Bailey, Jr., 1955 NW. Northrup St., Portland, Oreg. 97209

[21] Appl. No.: 603,523

[22] Filed: Oct. 25, 1990

[51] Int. Cl.⁵ .............. A61B 19/00; A61B 19/08; A61B 17/02
[52] U.S. Cl. .................. 128/849; 128/853; 128/20
[58] Field of Search .............. 128/849-856, 128/20

[56] References Cited

U.S. PATENT DOCUMENTS

| | | | |
|---|---|---|---|
| 1,230,873 | 6/1917 | Crossley | 128/20 |
| 3,054,398 | 9/1962 | Kobler | 128/20 |
| 3,397,692 | 8/1968 | Creager | 128/850 |
| 3,416,520 | 12/1968 | Creager | 128/850 |
| 3,435,821 | 4/1969 | Bennett | 128/853 |
| 3,650,267 | 3/1972 | Anderson | 128/853 |
| 3,824,998 | 7/1974 | Snyder | 128/856 |
| 4,037,589 | 7/1977 | McReynolds | 128/20 |
| 4,412,532 | 11/1983 | Anthony | 128/20 |
| 4,867,177 | 9/1989 | Urheim | 128/856 |

Primary Examiner—Michael A. Brown
Attorney, Agent, or Firm—Kolisch, Hartwell, Dickinson, McCormack & Heuser

[57] ABSTRACT

A drape for eye examination and surgery is provided for covering the anterior and interior surfaces of the eyelids. The drape includes a retainer, which in its preferred form is generally annular in shape. The retainer is insertable beneath the upper and lower eyelids and fits generally within the upper and lower palpebral sulci. A sheet of thin membrane material is attached to the retainer and extends peripherally outwardly from the retainer. When the retainer is in place on the eye, the sheet of membrane material covers the anterior and interior surfaces of the eyelids and simultaneously folds back the eyelashes. In the preferred embodiment of the drape the annular retainer is adjustable in size. Alternative shapes for the sheet of membrane material are disclosed. A method is also provided for installing and using the drape to cover the anterior and interior surfaces of the eyelids.

9 Claims, 2 Drawing Sheets

OPHTHALMOLOGIC DRAPE AND METHOD

BACKGROUND AND SUMMARY OF THE INVENTION

The present invention relates to ophthalmology and more particularly to an eye drape for covering body surfaces surrounding the eyeball and for protecting the eyeball during eye examination and surgery.

Surgical drapes are made in a wide variety of sizes and shapes for covering portions of the body. Drapes help maintain a sterile environment during surgery and help prevent foreign matter and organisms from entering the immediate vicinity of the surgery.

In ophthalmologic examination and surgery, eye drapes are frequently used to surround and protect the eyeball. One type of drape has a central hole or opening, the drape material being used to cover the portions of the body surrounding the opening. Another type of drape, the incise drape, is a continuous piece of sheet material which is placed over the eye and an opening is cut to expose the eye and surround it with the drape material. Both types of drapes can effectively cover the exterior of the eyelids and surrounding skin but cannot readily cover the interior surfaces of the eyelids. The eyelids and eyelashes are particularly important to cover because they represent a potential source of bacteria and other contaminates. Eyelid retractors, which pull the eyelids back from the eyeball, are used in many procedures, but it remains important to drape or cover the eyelids, even when retractors are used.

Covering the eyelids with a surgical drape usually occupies several minutes or longer at the start of a surgical procedure, requiring careful arrangement of the drape to cover surrounding body surfaces to the extent possible. In some cases, adhesive-backed drapes are used to cover problem areas such as eyelids. Nevertheless, even with the expenditure of time and great care, conventional drapes can only cover the exterior or exposed surfaces of the eyelids. They do not protect against bacteria and contaminates from the glands and membrane surfaces on the interior of the eyelids. Eyelashes present a similar challenges and must usually be covered, retracted or trimmed. To fully cover even the exterior surfaces of the eyelids and lashes remains a challenge.

It is an object of the present invention to provide a drape for covering the anterior and interior surfaces of the eyelids in order to protect the eyeball during examination and surgery. In particular, the drape of the present invention covers the interior of the eyelids and the eyelashes, together with the exterior of the eyelids and other surrounding body surfaces, thereby substantially reducing the risk of bacterial and other contamination from the eyelids.

It is a further object of the present invention to provide a drape for covering the anterior and interior surfaces of the eyelids which is retained in place surrounding the eyeball by a non-adhesive, generally annular member attached to the sheet material of the drape, reducing the reliance on adhesive surfaces in direct contact with the eyelids and thereby reducing the potential for contamination from failure of an adhesive.

It is a further object of the invention to provide a method of covering the anterior and interior surfaces of the eyelids by a process which includes installing a drape having a retainer which is shaped to generally surround the eyeball. The retainer extends beneath the upper and lower eyelids along the upper and lower palpebral sulci. After the retainer is installed, the portion of the drape which extends radially outwardly from the retainer is spread over those portions of the body surrounding the eyeball. In the preferred embodiment of the invention the retainer is adjustable in size so that it may be exactly conformed to the palpebral tissue of the eye being draped.

Accordingly, the invention provides a drape for covering the anterior and interior (i.e., posterior) surfaces of the eyelids, to protect the eyeball during examination and surgery. The drape comprises a retaining means which is insertable beneath the upper and lower eyelids for fitting generally within the upper and lower palpebral sulci. The drape further includes a sheet of thin, flexible membrane material generally surrounding the retaining means and attached thereto. The sheet extends from the retaining means over the eyelids and peripherally outwardly from the eyeball.

In a preferred form of the invention the retaining means is a unitary, deformable, retainer ring which is generally circular or elliptical and adjustable in size. It also includes a positioning arm extending radially outwardly from the retainer to facilitate installation and size adjustment. Alternative embodiments of the sheet material of the drape are provided, including a generally planar sheet extending circumferentially outwardly from the retainer and a sheet which includes additional fabric adjacent the edge where the sheet is joined to the retainer, for fitting beneath the eyelids.

The invention additionally includes a method of covering the anterior and interior (i.e., posterior) surfaces of the eyelids. The method employs the eye drape of the invention, including a retainer attached to flexible sheet material along the edge of the central opening. The drape is installed around the eyeball by inserting the retainer beneath the upper and lower eyelids, generally along the upper and lower palpebral sulci. The method of covering the eyelids further includes the step of spreading the drape radially outwardly from the eye, after the retainer is installed.

In its preferred form, the method of the invention, when used with a drape having a retainer which is adjustable in size, includes the step of inserting the retainer beneath the upper and lower eyelids while the retainer is sized smaller than its final adjusted size. The next step is then to increase the size of the retainer to a size which ensures that the retainer fits snugly beneath the eyelids along the upper and lower palpebral sulci. When the method is performed with an embodiment of the retainer which includes a positioning arm extending radially outwardly from the retainer, the step of installing the drape further includes positioning the drape around the eyeball with the positioning arm located generally over the outer canthus of the eye.

DETAILED DESCRIPTION OF THE PREFERRED EMBODIMENT

Figure 1:
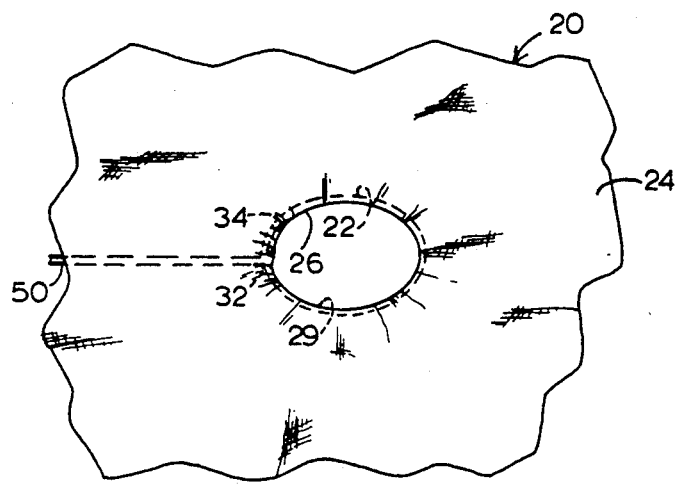
FIG. 1 is a partial, top plan view of a first embodiment of an eye drape in accordance with the present invention.

Referring to FIG. 1, an eye drape 20 is shown for covering the anterior and interior (i.e., posterior) surfaces of the eyelids during eye examination and surgery. The drape includes retaining ring 22, also referred to as retaining means insertable beneath the upper and lower eyelids. Retainer 22 is generally annular in shape, in the form of a ring or loop of deformable material such as plastic or metal.

Drape 20 also comprises a sheet 24 of flexible material, formed of any suitable fabric or sheet material which ca be sterilized and is capable of preventing the passage of liquids, particles or bacteria through its surface. A suitable material for sheet 24 is latex or another plastic material. Sheet 24 is for covering portions of the body surrounding the eye. The external perimeter (not shown) of sheet 24 is of any suitable size and shape, extending beyond the perimeter shown in FIG. 1. A suitable shape for sheet 24 would be rectangular or square, approximately six inches on a side. An opening 26 is formed in a central portion of sheet 24. Opening 26 will be generally circular or elliptical along its periphery, to surround the eye and correspond to the shape of retainer 22.

Figure 2:
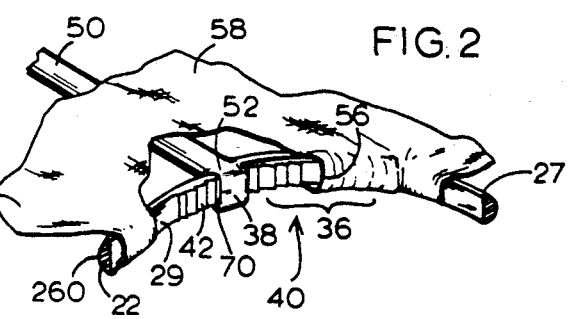
FIG. 2 is an enlarged, partial, perspective view of the drape of FIG. 1, partially cut away, illustrating the overlap portion of the elongated, curved member which forms the retainer of the drape, the locking device which sets the final, selected size of the retainer, and the positioning arm extending radially outwardly from the retainer.
Figure 3:
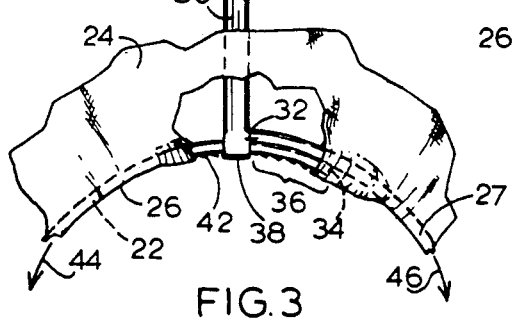
FIG. 3 is a top, partial, plan view, partially cut away, of the portion of the drape illustrated in FIG. 2.

Retainer 22 is attached to sheet 24 generally along the edge or periphery of central opening 26. Referring to FIGS. 1-3, retainer 22 is fabricated of resilient material such as plastic or metal, having a resiliency which allows it to be squeezed into an elongated, "out-of-round" or "out-up-elliptical" shape by relatively light finger pressure. Suitable materials for fabricating retainer 22 include polypropylene, poly-methylmethacrylate (also known as "PMMA"), Proline (trademark), or metal, such as stainless steel. Opening 26 in sheet 24 will have a general shape corresponding to that of retainer 22. Alternatively, retainer 22 can be thought of as having a central opening 29 along the inner periphery of the retainer corresponding to central opening 26 in flexible sheet 24.

In the first embodiment of the invention, retainer 22 is an elongated, curved member 27 having ends 32, 34 (see FIGS. 1-4) which extend adjacent one another in an overlap region 36. The size of retainer 22 is adjustable by changing the relative position of ends 32, 34 to change the circumferential dimension of the retainer. The first end 32 of the curved member includes a resilient band 38 which extends around the shank-portion 40 of the other end of the curved member, meaning the portion of curved member 27 adjacent or near second end 34. Band 38 flexibly engages cooperating ratchet teeth 42 formed on the inner periphery 29 of the retainer, on the shank portion 40 adjacent or near end 34. Band 38 and teeth 42 cooperatively form a locking means on retainer 22 for locking the overlapped ends of the retainer loop in selected positions relative to one another.

Ratchet interlock 38, 42 is a unidirectional locking means which permits enlargement of the retainer by increasing its circumference. Enlargement is effected by allowing shank portion 40 of curved member 27 to move in the direction of arrow 44 (FIG. 3), relative to first end 32. Relative movement of the ends 32, 34 in directions 44, 46, tends to enlarge the retainer by reducing the length of the overlap portion 36. The teeth 42 of the ratchet interlock are biased to permit only unidirectional relative movement of ends 32, 34 in the direction of arrows 44, 46, respectively. That permits the retainer to be expanded in size and automatically locks it at a selected size without the retainer subsequently slipping back to a smaller size.

Retainer 22 also includes a positioning arm 50 attached to the retainer adjacent first end 32 of curved member 27. Arm 50 extends radially outwardly from the retainer and is positioned beneath flexible sheet material 24. In the preferred embodiment, arm 50 extends outwardly from first end 32 of the curved member and ratchet band 38 extends inwardly from the first end. Ratchet band 38 thus forms an eyelet on the inner end 52 of arm 50, with shank portion 40 passing through the eyelet. Positioning arm 50 serves as a convenient anchor point which can be grasped by the physician during installation of the drape, to both position the drape and assist in the expansion of the size of retainer 22. Arm 50 is preferably integral with retainer 22, formed of the same resilient material.

Sheet material 24 is bonded to retainer 22 along the entire edge or periphery of central opening 26. Except for the overlap portion 36 and adjacent regions where size adjustment is effected, the flexible sheet material is preferably bonded to retainer 22 by heat sealing or adhesive. In the region where the ends of curved member 27 overlap, flexible sheet material 24 is attached to retainer 22 by encirclement of the curved member, as shown most clearly in FIG. 2. The sheet material in the overlap region of the retainer forms a generally tubular or tunnel-shaped, loose-fitting connection, which surrounds the elongated member 27 and allows for expandability of the retainer, while retaining the integrity of sheet 24. Termed an expandable attachment 56, the encircling, tunnel-shaped portion provides a secure slidable connection to curve member 27. The expandable attachment 5 is preferably sealed to band 38 and provided with a suitable sealed encirclement of arm 50 which will allow arm 50 to pass through the slidable connection, whereby the arm remains beneath the principal expanse 58 of the sheet material 24, radially outside retainer 22 (FIG. 2). Expandable attachment 56 accommodates adjustments in the size of the retainer without breaking or tearing the sheet material.

Figure 4:
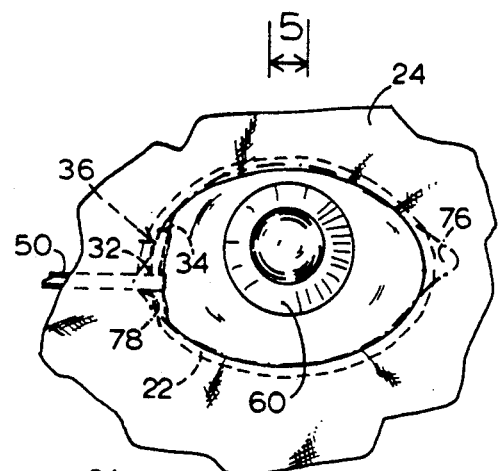
FIG. 4 is a partial, top plan view of the eye drape of FIG. 1 in place on an eye covering the anterior and interior surfaces of the eyelids.
Figure 5:
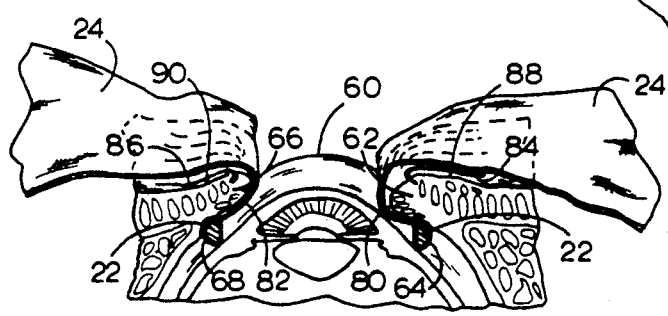
FIG. 5 is a side, partially cross-sectional and partially perspective view of a slice through a central portion of the eye shown in FIG. 4, taken approximately between parallel section lines 5—5, and showing the approximate location of the drape and retainer in place on an eye.

Referring to FIGS. 4 and 5, retainer 22 is insertable beneath the upper and lower eyelids of an eye 60. When inserted, retainer 22 will rest within, and generally conform to, the upper and lower palpebral sulci of the eye. The sulcus of each eyelid (upper and lower) extends along the line where the interior surface of the eyelid joins the attaching tissue surrounding the eyeball. Each sulcus is at the interior root of the eyelid, representing the furthest extent an object can be inserted beneath the eyelid without piercing the tissue. In FIG. 5, which is a narrow slice of eye 60 between lines 5—5 of FIG. 4, the sulcus of upper eyelid 62 is at 64, along the line where the underside of the eyelid joins the eye. The sulcus of lower eyelid 66 is at 68.

To install drape 20 on eye 60, the physician or surgeon will select a drape which has been packaged under sterile conditions, and will employ the method of the present invention for draping an eye. The method employs the above-described drape 20. A packaged drape will be manufactured with the retainer 22 at a starting size which will generally be the smallest adjustable size of the retainer. In other words, retainer 22 will be supplied for insertion around an eye with the maximum overlap between the first and second ends 32, 34 of curved member 27 so that it may later be expanded in size. Having the retainer sized smaller than its final adjusted size facilitates insertion. The physician or surgeon will position the retainer on the eye, generally surrounding the eyeball, beneath the upper and lower eyelids. The actual technique of installation will include deforming or squeezing the retainer 22 into a somewhat elongated or compressed shape and each eyelid will be raised or retracted so the retainer can be inserted beneath the eyelids. Then, holding positioning arm 50, the "free" end 36 of curved member 27 will be drawn through encircling ratchet band 38 to increase the size of the retainer. This will be accomplished by grasping and pulling the loop outwardly in direction 44 (FIG. 3) at a point near shank portion 40. As the loop expands, ratchet teeth 42 pass through and beneath band 38 which engages each tooth in the well-known manner of a ratchet. The inclined surfaces of the teeth lift the tooth-engaging edge 70 of band 38 (FIG. 2) over each successive tooth. As the loop is expanded in size, the ratchet locks the retainer and prevents it from returning to a smaller size. Accordingly, the locking ratchet 38, 42 engages the shank portion 40 of curved member 27, and locks the ends 32, 34 in their respective relative positions when the retainer has reached the appropriate size.

In order to effectively employ positioning arm 50 on the retainer without having it interfere with the functioning of the drape, arm 50 is preferably positioned as shown in FIG. 4. The eye 60 shown in FIG. 4 is the right eye of the patient, with the forehead located above the eye and the nose to the right. As such, the inner canthus of the eye 76 is on the right of the eyeball and the outer canthus 78 on the left. Positioning arm 50 is preferably positioned radially around the eyeball so that the positioning arm is located generally over outer canthus 78. That, in turn, positions the overlapped portions 36 of curved member 27 approximately adjacent the inner canthus as well. To complete insertion of retainer 22, with the retainer held by positioning arm 50 in the above-described selected position, the retainer is expanded by pulling curved member 27 adjacent shank portion 40, which causes ratchet locking means 38, 42 to continuously engage the shank portion. As a result, the ratchet is engaged and holds the retainer at a fixed size when it has been expanded to the correct size.

Once installed on the eye, with the retainer enlarged, as described above, the retainer fits snugly beneath the eyelids along the upper and lower palpebral sulci 64, 68 of eye 60. Referring to FIG. 5, retainer 22 occupies the palpebral tissue along a path extending within the upper and lower palpebral sulci and also overlies the inner and outer canthi 76, 78, respectively (FIG. 4). After the retainer has been installed on the eye, flexible sheet 24 is spread radially outwardly from the eye, thereby covering the anterior and interior surfaces of the eyelids.

Describing the relative positions of the drape and parts of the eye with reference to FIG. 5, retainer 22, when in place on eye 60, generally surrounds the eyeball and sheet 24 covers the inner surfaces of the eyelids 80, 82, the lashes 84, 86 and the outer surfaces of the eyelids 88, 90. Discussing each eyelid separately, sheet 24 extends from retainer 22 along the underside of upper eyelid 62, covering the posterior (interior) surface 80 of the eyelid, and extending around and over the outer (anterior) surface 88 of the eyelid. As such, sheet 24 covers the anterior and interior surfaces of the eyelid. Upper eyelashes 84 are also covered by sheet 24, which tends to fold them back away from the eyeball Sheet 24 also extends from retainer 22 along the underside of lower eyelid 66, covering the posterior (interior) surface 82 of the eyelid and extending around and over the outer (anterior) surface 90 of the eyelid. Lower eyelashes 86 are also covered by sheet 24, which tends to fold them back away from the eyeball.

Figure 6:
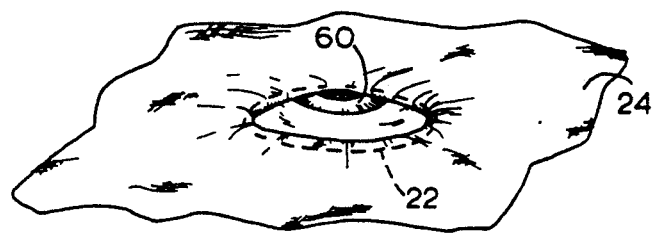
FIG. 6 is a partial, perspective view of the eye drape in place on an eye, as shown in FIGS. 4 and 5, on a smaller scale.

FIG. 6 shows the approximate appearance of the eyeball 60 with retainer ring 22 in place beneath the upper and lower eyelids and with sheet 24 folded back peripherally outwardly from the eyeball. As can be seen, drape 20 completely covers the eyelashes, holding them away from the eyeball. Drape 20 also affords complete coverage of the interior and anterior surfaces of the eyelids, reducing the chance of bacterial contamination from the glands and surfaces on the interior of the eyelids. Retainer 22 generally secures drape 20 to the eye, reducing or eliminating the need for adhesives to hold the drape in place on the eye, except, perhaps, at the outer perimeter of sheet 24 (not shown). The final shape of retainer 22, once it is installed on the eye, generally assumes the shape of the upper and lower palpebral sulci and thus will be generally elliptical in shape. That is true even if retainer 22, prior to installation, was circular.

Figure 7:
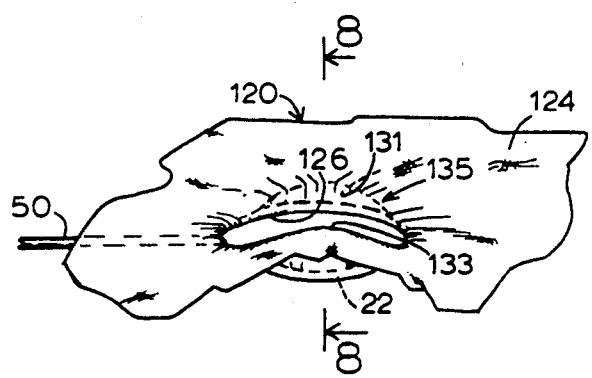
FIG. 7 is a partial, perspective view, partially cut away, of an embodiment of the eye drape which includes additional flexible sheet material for extending beneath the eyelids.
Figure 8:
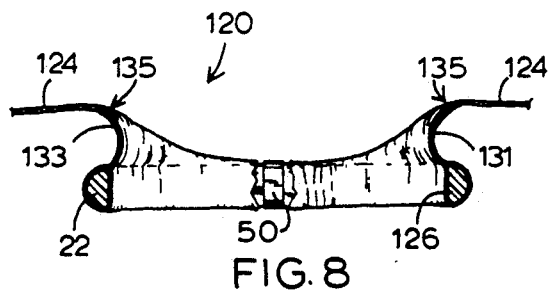
FIG. 8 is a side, cross-sectional view of the embodiment of FIG. 7, taken along line 8—8 of FIG. 7.

The first embodiment of eye drape 20 in accordance with the present invention shown in FIGS. 1–6, has sheet material 24 which is generally flat or planar and extends radially outwardly from retainer 22. FIG. 7 shows an embodiment of the drape 120 which has a retainer 22 with the same configuration as in the first embodiment. The sheet material 124 in this embodiment of drape 120 differs from the first embodiment in that additional flexible sheet material is added to sheet 124 in a first annular region 135 adjacent the central opening 126, for extending beneath and covering the underside of the eyelids. The additional flexible sheet material includes a pair of ridges or folds 131, 133 on opposite sides of the retainer. Folds 131, 133 are added for the purpose of providing additional sheet material where it is required to reduce creasing and folding of the sheet material around the eye. Folds 131, 133 are oriented on opposite sides of an axis of symmetry extending generally along positioning arm 50 and through the center of retainer 22. Since arm 50 is to be positioned overlying the outer canthus of the eye, folds 131, 133 will be properly oriented to extend beneath the upper and lower eyelids, respectively. FIG. 8 illustrates the shape of folds 131, 133 in a cross-sectional view taken along line 8—8 of FIG. 7. As can be seen, folds 131, 133 are curved, generally underbeveled, hyperboloid-shaped areas contoured to conform to the eyelids.

Figure 9:
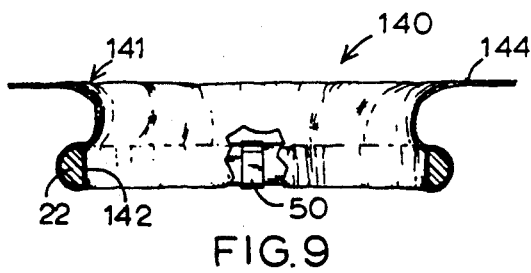
FIG. 9 is a side, cross-sectional view, as in FIG. 8, of another embodiment of an eye drape which includes additional flexible sheet material, completely encircling the retainer, for extending beneath the eyelids.

Another alternative embodiment of the eye drape of the present invention is illustrated in FIG. 9. In this embodiment, drape 140, like drape 120, includes additional flexible material for extending beneath and covering the underside of the eyelids in a first annular region 141 adjacent the central opening 142 of the drape. Unlike the embodiment of drape 120, just described, the additional flexible material in the embodiment shown in FIG. 9 provides additional sheet material around the entire periphery of retainer 22. In both the embodiment of FIGS. 7 and 8, and the embodiment of FIG. 9, the sheet material 144 extending radially outwardly from the first annular region adjacent the central opening is generally planar or flat.

Figure 10:
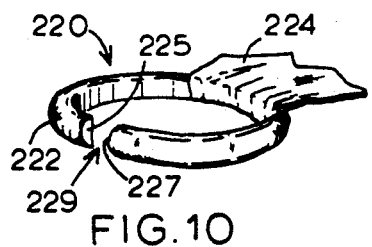
FIG. 10 is a partial, perspective view, with the flexible sheet material partially cut away, of an embodiment of the eye drape which includes a resilient retainer having an open loop generally in the shape of the letter "C".
Figure 11:
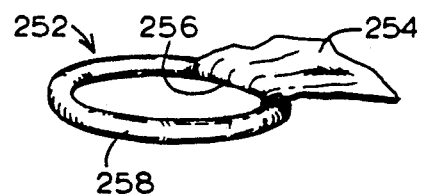
FIG. 11 is a partial, perspective view as in FIG. 10, with the flexible sheet material partially cut away, showing another embodiment of the eye drape in which the retainer is a closed, annular ring.

Other alternative embodiments of the eye drape of the present invention are shown in FIGS. 10 and 11. These embodiments employ different configurations of retainer 22 within the scope of the invention. FIG. 10 shows an eye drape 220 with most of the sheet material surrounding the retainer ring cut away to illustrate this embodiment. In fact, the sheet material completely surrounds the retainer as in the first embodiment. In the embodiment of FIG. 10 a retainer 222 is an elongated curved member having ends 225, 227 which do not overlap. The ends act as means forming a gap 229 in the circumference of the retainer. Retainer 222, like the first embodiment, is formed of a resilient material which is deformable. Flexible sheet material 224, attached to and encircling retainer 222, extends across gap 229. A suitable tubular sleeve portion can be provided on sheet 224, like portion 56 of the first embodiment, in the region of the sheet material bridging gap 229. The remainder of sheet 224 is attached to retainer 222 by heat sealing or the like, as in the first embodiment.

Installation of the embodiment of FIG. 10 is similar to the first embodiment, except that the retainer is first squeezed down to a smaller size or diameter as the retainer is installed on an eye. The squeezing of retainer 222 is preferably accomplished by finger pressure or by a suitable instrument. Once the retainer is generally in place on the eye, with the retainer installed beneath the upper and lower eyelids, the compressing pressure is released and the retainer springs back to its fully expanded shape as shown in FIG. 10. Assuming a retainer of the correct size is used meaning that its size in its expanded, released state corresponds generally to the dimensions of the palpebral sulci of the eye, the retainer will fit snugly within the upper and lower palpebra sulci in the manner shown in FIG. 5. In the embodiment of FIG. 10, it is suggested that gap 229 be oriented to overly the outer or inner canthus of the eye, to avoid the possibility of pinching the palpebral tissue within gap 229. Once retainer 222 is installed around the eye, flexible sheet 224 is spread radially outwardly in the manner of the first embodiment, covering the interior and anterior surfaces of the eyelids and spreading the eyelashes outwardly from the eyeball.

Another embodiment of the eye drape of the present invention is shown in FIG. 11. Like the previously-described embodiment, the embodiment shown in FIG. 11 includes an eye drape of flexible sheet material 254 which has a central opening therethrough, mostly cut away in the illustration of FIG. 11 to better show the retainer 258. Sheet material 254 completely surrounds retainer 258, leaving a central opening 256 therein through which eye examination and surgery is conducted. Retainer 258 extends around and is attached to central opening 256 along its edge by heat sealing or another suitable method. Unlike the previous embodiments, there need be no provision for a tubular portion such as expandable attachment 56 in FIG. 2 because retainer 258 is not adjustable in size. Other than that difference in attachment, sheet material 254 is like the sheet material 24 in the first embodiment.

Retainer 258 in the embodiment of FIG. 11, also referred to as retaining means insertable beneath the upper and lower eyelids, is an annular ring. It is formed of the same resilient material as ring 22 in the first embodiment. Unlike the first embodiment, retainer 258 is a unitary continuous annular device. Because the retainer is not adjustable in size to exactly fit an eye, drape 252 will be made available in a variety of sizes to accommodate eyes having palpebral tissue of different sizes. Assuming that a retainer 258 of the correct size is selected, the retainer will extend along the upper and lower palpebral sulci, overlying the inner and outer canthi of the eye, once it is installed on the eye. As such, eye drape 252 should function in the same manner as drape 20 of the first embodiment.

The method of installing eye drape 252 in the embodiment of the FIG. 11 will include selecting a drape having a retainer of the correct size. A preliminary step performed by the physician or surgeon will be to measure the eye and select, from a range of drapes, a drape having a retainer of the size desired. The retainer will then be inserted beneath the upper and lower eyelids. Assuming a proper fit, retainer 258 should assume the position shown for retainer 22 in FIG. 5, namely, fitting snugly within the upper and lower palpebral sulci 64, 68, respectively. After installation of retainer 258, sheet material 254 is spread radially outwardly from the eye, covering the anterior and interior surfaces of the eyelids, as well as the eyelashes. Once in place on the eye, drape 252 in the embodiment of FIG. 11 should look exactly like the illustration in FIG. 6.

Both the embodiments 220, 252 shown in FIGS. 10 and 11, respectively, can be provided with sheet material which is either generally planar, as shown in FIG. 1, or includes additional sheet material in a first annular region adjacent the central opening of the drape, as in FIGS. 7, 8 and 9.

The overall cross-sectional shape of the curved member 27 forming retainer 22 is shown, for the embodiments of FIGS. 1-10, as generally semi-circular. That shape, which in cross-section looks like a "D," is particularly suitable for the first embodiment of the drape, which because it includes a flat inner surface along the inside edge 29, which facilitates the positioning of ratchet teeth 42 on shank portion 40. The rounded outer edge 260 (FIG. 2) of the retainer helps eliminate sharp corners or edges which might injure the palpebral tissue. Other cross-sectional shapes for the retainer are possible within the scope of the present invention. The embodiment of FIG. 11 is illustrated with retainer 258 having a generally circular cross-section. Alternatively, the retainer in all the embodiments could have a generally rectangular cross-section to provide a retainer which is generally hoop-shaped. Thus, the shape of the curved member which forms the annular retainer may be of any suitable cross-sectional configuration.

Removal of the eye drape from the eye, after completion of eye examination or surgery, is accomplished either by retracting the eyelids far enough to remove the retainer or by cutting the retainer to facilitate removal. It is anticipated that the retainer generally will be cut at a point along its length, preferably at a point overlying the inner or outer canthus, to allow easy removal without abrasion of the palpebral tissue. In certain procedures it may also be desirable for the physician or surgeon to cut off and remove positioning arm 50 during or after installation of the drape.

The various embodiments of an eye drape in accordance with the present invention provide a convenient means for covering the anterior and interior surfaces of the eyelids, as well as the eyelashes, to protect the eyeball during examination and surgery. The drape may be used in conjunction with conventional eyelid retractors which pull back the eyelids to further expose the eyeball. In certain circumstances, drape sheet material 24 may assist in retracting the eyelids by a proper positioning and securing of the sheet material as it is folded back over the eyelids and pulled outwardly from the eyeball. It is anticipated that drapes fabricated in accordance with the present invention will be available in several sizes and in order to conform to particular examination or surgical requirements for individual eyes.

Although the first embodiment retainer 20 is shown with a ratchet-type locking means for locking the overlapping portions of the retainer loop in selected positions relative to one another, other types of locking means could be used. For example, a frictional engagement which permits both enlargement and reduction in the size of the retainer loop could be provided. The enlargement-only type of locking means used with the first embodiment is considered preferable because it eliminates inadvertent slippage which might loosen the retainer during a surgical procedure. The exact type of locking means used with the drape of the present invention is, nevertheless, a matter of design choice.

Alternative forms of flexible sheet 24 are also possible within the scope of the present invention. Although the embodiments shown and described employ sheets 24 which are each a continuous expanse of thin membrane material having an opening centrally disposed therein, sheet 24 could include one or more slits extending radially outwardly from retainer 28. Such slits might be useful in certain applications where access beneath the sheet material is required, such as for access to positioning arm 50. Sheet 24 could also be formed in separate, multiple segments, joined together, although it is anticipated that unitary construction will be preferable due to ease of manufacture and the need to maintain a sterilized, impenetrable barrier.

Although the actual dimensions of a drape formed in accordance with the present invention should be in conformance with the requirements of the range of eyes to be examined, some numerical guidelines will be helpful in visualizing the dimensions of the drape. The curved, elongated member which, when formed into a closed loop having overlapping ends, forms retainer 22, will preferably have an overall length of between 5 and 10 centimeters and a thickness of between 2 millimeters and 10 millimeters. When formed into a loop, the elongated member will have an inner diameter of between 14 millimeters and 30 millimeters. It is anticipated that overall adjustability will be achieved by an overlap region 36 of approximately 1 centimeter in length. Drapes in accordance with the embodiments of FIGS. 10 and 11 will have retainers which range in size between 14-millimeters and 30-millimeters, inside diameter, and between 2-millimeters, and 10 millimeters in thickness. Such a dimensional range should provide drapes which will be appropriate for most human eyes. The exterior dimension of flexible sheet 24, along its outer perimeter, is a matter of design choice and will be determined by the procedure being performed.

The eye drape of the present invention significantly improves the coverage of the eyelids and protection of the eyeball during examination and surgery, as compared with conventional prior art drapes. In particular, the drape of the present invention covers the interior (i.e., posterior) surfaces of the eyelids, which are a source of bacteria and other contaminates. The drape also conveniently and effectively covers the eyelashes, folding them back on the eyelids and away from the eyeball, reducing the potential for contamination and eliminating the need to trim or otherwise remove the eyelashes during examination and surgery. As such, the invention facilitates eye examination and surgery by means of a device that can be manufactured at relatively modest cost. It is anticipated that drapes in accordance with the present invention will be prepackaged in sterilized packets or the like and provided in a sterile condition, ready for use.

The invention provides a drape for covering the anterior and interior surfaces of the eyelids during examination and surgery, in order to protect the eyeball. The drape covers the interior of the eyelids and the eyelashes, together with the exterior of the eyelids and surrounding surfaces, thereby reducing the risk of bacterial contamination from beneath the eyelids. The invention provides a drape which is retained in place, surrounding the eyeball, by a non-adhesive, generally annular member attached to the sheet material of the drape. Adhesives need not be used to secure the drape to the eyelids, thereby reducing the potential for contamination of the eyeball during surgery from failure of an adhesive. The invention additionally provides a method of covering the anterior and interior surfaces of the eyelids to protect the eyeball during eye examination and surgery by a process which includes installing a drape of the present invention on the eye. The drape has a retainer shaped to generally surround the eyeball beneath the upper and lower eyelids along the upper and lower palpebral sulci. Steps in the method of the invention include spreading the portion of the drape which extends radially outwardly from the retainer out over those portions of the body which surround the eye. The method results in a drape in place to protect the eyeball from potential contamination from regions beneath the eyelids, as well as from surrounding body regions.

What is claimed is:

1. A drape for covering the anterior and interior surfaces of the eyelids to protect the eyeball during examination and surgery, comprising:

an expanse of flexible sheet material having a central opening therein through which eye examination and surgery is conducted, a retainer extending around said central opening and attached to said flexible sheet material for fitting beneath the upper and lower eyelids along the upper and lower palpebral sulci, said retainer being in the form of an elongated, curved member having ends which extend adjacent one another, the size of said retainer being adjustable by changing the relative positions of said ends of said curved member thereby changing the circumferential dimension of the retainer, wherein said expanse of flexible sheet material extends beneath and covers the underside of the eyelids when said retainer is in place beneath the upper and lower eyelids, such that said flexible sheet material projects the eyeball from contaminates on the underside of the eyelids, and a positioning arm attached to said retainer adjacent one end of said curved member and extending radially outwardly therefrom beneath said flexible sheet material.

2. A drape for covering the anterior and interior surfaces of the eyelids to protect the eyeball during examination and surgery, comprising:

a sheet of flexible material for covering portions of a body surface surrounding the eye, said sheet having a central opening therein through which eye examination and surgery is conducted, said flexible sheet material including a first annular region extending upward from said central opening to a section of said sheet material having a planar surface geometry, said first annular region including additional flexible sheet material for extending beneath and covering the underside of the eyelids and said section having a generally planar surface geometry being outside said first annular region, and a retainer extending around said central opening and attached to said first annular region of said sheet material for fitting beneath the upper and lower eyelids along the upper and lower palpebral sulci, whereby said retainer holds said sheet material in place beneath the eyelids for spreading outwardly from the eyeball to cover the anterior and interior surfaces of the eyelids.

3. A drape for covering the anterior and interior surfaces of the eyelids to protect the eyeball during examination and surgery, comprising:

retaining means insertable beneath the upper and lower eyelids for fitting generally within the upper and lower palpebral sulci, said retaining means being an elongated, curved member having ends which extend adjacent one another to form an expandable loop which is adjustable in length to change the size of said retaining means, the length of said retaining means being adjusted by changing the relative positions of said ends to change the circumferential dimension of said loop, and including means for locking the ends of the curved member in selected positions relative to one another whereby the size of said retaining means is selectively fixed, an expanse of flexible sheet material surrounding said retaining means and attached thereto for completely covering the underside of the eyelids when said retaining means is in place beneath the upper and lower eyelids, whereby said flexible sheet material protects the eyeball from contamination originating on the interior surfaces of the eyelids, and a positioning arm attached to said retaining means adjacent one end of said curved member and extending radially outwardly therefrom beneath said flexible sheet material.

4. A drape for covering the anterior and interior surfaces of the eyelids to protect the eyeball during examination and surgery, comprising:

retaining means insertable beneath the upper and lower eyelids for fitting generally within the upper and lower palpebral sulci, said retaining means being annular in shape, and an expanse of flexible sheet material surrounding said retaining means and attached thereto for completely covering the underside of the eyelids when said retaining means is in place beneath the upper and lower eyelids, whereby said flexible sheet material protects the eyeball from contamination originating on the interior surfaces of the eyelids, said flexible sheet material including a central opening and first annular region adjacent said central opening which includes additional flexible sheet material for extending beneath and covering the underside of the eyelids, said flexible sheet material further including a generally planar surface geometry outside said first annular region.

5. In eye examination and surgery, a method of draping an eye to protect the eyeball, comprising:

installing a retainer which is annular in shape and attached to a drape made of flexible sheet material which extends around the retainer such that the retainer surrounds the eyeball and fits beneath the eyelids generally along the upper and lower palpebral sulci, such that the drape completely covers the underside of the eyelids when the installing step is completed and the retainer is in place beneath the upper and lower eyelids, whereby the flexible sheet material protects the eyeball from contamination originating on the interior surfaces of the eyelids, and then spreading the drape radially outwardly from the eye, thereby covering both the anterior and interior surfaces of the eyelids.

6. A method as in claim 5 in which the retainer of the drape is adjustable in size to change the circumferential length of the retainer, the step of installing the drape including inserting the retainer beneath the upper and lower eyelids while the retainer is sized smaller than its final adjusted size and then increasing the size of the retainer to ensure that the retainer fits snugly beneath the eyelids along the upper and lower palpebral sulci.

7. A method as in claim 6 in which the retainer is in the form of an elongated, curved member having ends which extend adjacent one another, further including locking means for locking the ends of the curved member in selected relative positions and including a positioning arm attached to the retainer adjacent one end of the curved member and extending outwardly therefrom, said step of increasing the size of the retainer includes holding the retainer in a selected position with the positioning arm, expanding the retainer by pulling the curved member near the end opposite said one end, and engaging said locking means when the retainer has reached the correct size.

8. A method as in claim 6 in which the retainer includes a positioning arm extending radially outwardly therefrom, said step of installing the drape further including positioning the drape around the eyeball with the positioning arm located generally over the outer canthus.

9. In eye examination and surgery, a method of covering the anterior and interior surfaces of the eyelids to protect the eyeball, comprising:

determining, for the eye to be examined, the approximate dimensions of an annular pathway extending around the eyeball, extending within the upper and lower palpebral sulci and extending over the inner and outer canthi, selecting a drape having a central opening and an annular retainer attached to the drape along the edge of the central opening from a plurality of said drapes, each drape in the plurality of drapes having a retainer of a different size, wherein each drape is formed of flexible sheet material, and the drape selected in the selecting step has a retainer which generally corresponds in its dimension to the dimensions of the annular pathway, installing the retainer attached to the selected drape beneath the upper and lower eyelids generally along the upper and lower palpebral sulci, and spreading the drape radially outwardly from the eye, thereby covering the anterior and interior surfaces of the eyelids.

* * * * *